United States Patent
Xu et al.

(10) Patent No.: US 10,997,475 B2
(45) Date of Patent: May 4, 2021

(54) COPD CLASSIFICATION WITH MACHINE-TRAINED ABNORMALITY DETECTION

(71) Applicant: Siemens Healthcare GmbH, Erlangen (DE)

(72) Inventors: Zhoubing Xu, Plainsboro, NJ (US); Shikha Chaganti, Nashville, TN (US); Sasa Grbic, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 105 days.

(21) Appl. No.: 16/275,780

(22) Filed: Feb. 14, 2019

(65) Prior Publication Data

US 2020/0265276 A1    Aug. 20, 2020

(51) Int. Cl.
| | |
|---|---|
| *G06K 9/66* | (2006.01) |
| *G06K 9/00* | (2006.01) |
| *G06T 11/00* | (2006.01) |
| *G06T 7/00* | (2017.01) |
| *A61B 6/03* | (2006.01) |
| *A61B 6/00* | (2006.01) |

(Continued)

(52) U.S. Cl.
CPC ............... *G06K 9/66* (2013.01); *A61B 5/085* (2013.01); *A61B 5/7267* (2013.01); *A61B 6/032* (2013.01); *A61B 6/466* (2013.01); *A61B 6/5235* (2013.01); *G06K 9/00201* (2013.01); *G06T 7/0012* (2013.01); *G06T 11/003* (2013.01); *G06T 2207/10072* (2013.01); *G06T 2207/20081* (2013.01); *G06T 2207/20084* (2013.01); *G06T 2207/30061* (2013.01)

(58) Field of Classification Search
CPC .. G06K 9/66; A61B 6/50; A61B 6/484; A61B 6/461; A61B 6/5252; G06T 7/11; G06T 7/50; G06T 7/0012; G06T 2207/30061; G06T 2207/10116
USPC ........................................................ 382/131
See application file for complete search history.

(56) References Cited

U.S. PATENT DOCUMENTS

| | | | |
|---|---|---|---|
| 10,258,304 B1 * | 4/2019 | Kiraly ................ | A61B 6/504 |
| 2018/0068446 A1 * | 3/2018 | Ross .................... | G06T 7/136 |

(Continued)

OTHER PUBLICATIONS

Batmanghelich, Nematollah K., et al. "Generative method to discover genetically driven image biomarkers." International Conference on Information Processing in Medical Imaging. Springer, Cham, Jul. 2015.

(Continued)

*Primary Examiner* — Congvan Tran

(57) ABSTRACT

For COPD classification in a medical imaging system, machine learning is used to learn to classify whether a patient has COPD. An image-to-image network deep learns spatial features indicative of various or any type of COPD. The pulmonary function test may be used as the ground truth in training the features and classification from the spatial features. Due to the high availability of pulmonary function test results and corresponding CT scans, there are many training samples. Values from learned features of the image-to-image network are then used to create a spatial distribution of level of COPD, providing information useful for distinguishing between types of COPD without requiring ground truth annotation of spatial distribution of COPD in the training.

20 Claims, 4 Drawing Sheets

(51) Int. Cl.
    *A61B 5/085*    (2006.01)
    *A61B 5/00*     (2006.01)

(56) References Cited

U.S. PATENT DOCUMENTS

| | | | | |
|---|---|---|---|---|
| 2018/0137244 | A1* | 5/2018 | Sorenson | G16H 30/20 |
| 2018/0192987 | A1* | 7/2018 | Salgo | G16H 50/30 |
| 2018/0271465 | A1* | 9/2018 | Proksa | G06T 7/11 |
| 2019/0122073 | A1* | 4/2019 | Ozdemir | A61B 6/5217 |
| 2019/0164642 | A1* | 5/2019 | Hartung | G06N 3/0454 |
| 2019/0266486 | A1* | 8/2019 | Yamada | G06K 9/4652 |
| 2019/0371450 | A1* | 12/2019 | Lou | G16H 50/30 |
| 2020/0281543 | A1* | 9/2020 | Sahbaee Bagherzadeh | A61B 6/032 |

OTHER PUBLICATIONS

Christodoulidis, Stergios, et al. "Multi-source transfer learning with convolutional neural networks for lung pattern analysis." arXiv preprint arXiv:1612.02589 (2016).

Diaz, Alejandro A., et al. "Airway count and emphysema assessed by chest CT imaging predicts clinical outcome in smokers." Chest 138.4 (2010): 880-887.

Galbán, Craig J., et al. "Computed tomography-based biomarker provides unique signature for diagnosis of COPD phenotypes and disease progression." Nature medicine 18.11 (Nov. 2012): 1711-1715.

Gangeh, Mehrdad J., et al. "A texton-based approach for the classification of lung parenchyma in CT images." International Conference on Medical Image Computing and Computer-Assisted Intervention. Springer, Berlin, Heidelberg, 2010.

Hosseini, M. Parsa, H et al. "A novel method for identification of COPD in inspiratory and expiratory states of CT images." Biomedical Engineering (MECBME), 2011 1st Middle East Conference on. IEEE, 2011.

Martinez, Carlos H., et al. "Relationship between quantitative CT metrics and health status and BODE in chronic obstructive pulmonary disease." Thorax 67.5 (May 2012): 399-406.

Matsuoka, Shin, et al. "Quantitative CT measurement of cross-sectional area of small pulmonary vessel in COPD: correlations with emphysema and airflow limitation." Academic radiology 17.1 (2010): 93-99.

Rambod, Mehdi, et al. "Six-minute walk distance predictors, including CT scan measures, in the COPDGene cohort." Chest 141.4 (Apr. 2012): 867-875.

Schroeder, Joyce D., et al. "Relationships between airflow obstruction and quantitative CT measurements of emphysema, air trapping, and airways in subjects with and without chronic obstructive pulmonary disease." American Journal of Roentgenology 2013 (Sep. 2013): W460-W470.

Sorensen, Lauge, et al. "Texture-based analysis of COPD: a data-driven approach." IEEE transactions on medical imaging 31.1 (Jan. 2012): 70-78.

* cited by examiner

COPD CLASSIFICATION WITH MACHINE-TRAINED ABNORMALITY DETECTION

BACKGROUND

The present embodiments relate to chronic obstructive pulmonary disorder (COPD) classification. COPD is an obstructive lung disease caused due to poor airflow. Two main underlying causes for COPD are emphysema and airway disease. COPD is generally diagnosed by a pulmonary function test using a breathing tube. The main outputs of functional pulmonary test are Forced Expiratory Value in 1 second (FEV1) and Forced Vital Capacity (FVC). These values are normalized based on demographic distribution, and a GOLD score, a score of severity of COPD, is calculated, where GOLD 0: FEV1/FVC>0.7 (no COPD); GOLD 1 (Mild/Risk of COPD): FEV1/FVC<0.7 and FEV1>0.8; GOLD 2 (Moderate COPD): FEV1/FVC<0.7 and 0.79>FEV1>0.5; GOLD 3 (Moderate-Severe COPD): FEV1/FVC<0.7 and 0.5>FEV1>0.3; and GOLD 4 (Severe COPD): FEV1/FVC<0.7 and 0.3>FEV1. The pulmonary function change can be attributed to several different conditions such as bronchitis and asthma, so does not provide for a complete diagnosis.

A computed tomography (CT) scan of the lung is used to confirm the diagnosis. Emphysema is the destruction of lung tissue, which is detectable on high-resolution CT scans. Emphysema is characterized by gross regions of low-attenuation (<−950 Hounsfield units) on inspiratory CT scans. Airway disease is characterized by bronchial wall thickening, which is also visible on high-resolution CT scans. COPD is also characterized by various other structural changes visible on a CT scan, such as changes in vasculature. Annotation of these multiple structural changes on a CT is time-consuming and difficult to establish. Usually, simple metrics such as percentage of low-attenuation area are used to characterize the CT scans. These measurements are sufficient in detecting severe COPD but miss detection of mild and moderate cases, which have subtle CT characteristics.

Imaging biomarkers are used for identification of COPD in prognosis prediction and therapy management. Structural changes visible on CT are correlated with prognostic factors and symptoms of COPD. Studies show correlation, but do not demonstrate predictive capabilities, of these imaging biomarkers. Automated detection focuses on identification of emphysema and classification of types of emphysema by using texture-based features in the CT scan. Emphysema only accounts a portion of COPD. In a machine learning approach, relative differences between inspiratory and expiratory may be useful in identifying regions of the lung affected by emphysema, airway disease or both. However, accurate identification or even information useful to guide identification is elusive due to a limited amount of annotated datasets distinguishing between types of COPD in CT scans.

SUMMARY

By way of introduction, the preferred embodiments described below include methods, computer readable media, and systems for COPD classification in a medical imaging system. Machine learning is used to learn to classify whether a patient has COPD. An image-to-image network deep learns spatial features indicative of various or any type of COPD. The pulmonary function test may be used as the ground truth in training the features and classification from the spatial features. Due to the high availability of pulmonary function test results and corresponding CT scans, there are many training samples. Values from learned features of the image-to-image network are then used to create a spatial distribution of level of COPD, providing information useful for distinguishing between types of COPD without requiring ground truth annotation of spatial distribution of COPD in the training.

In a first aspect, a method is provided for COPD classification in a medical imaging system. A medical scanner scan lungs of a patient. The scan provides first imaging data representing a multi-dimensional region of the lungs of the patient. The imaging data is scan data to be used for imaging or data formatted for display. An image processor applies a machine-learned generative network to the first imaging data. The machine-learned generative network was trained to output the COPD classification. An activation map is generated from values of features from the machine-learned generative network. The activation map represents a level of COPD by location within the multi-dimensional region. An image from the activation map is output on a display.

In one embodiment, a CT system scans a three-dimensional region, and the activation map is a three-dimensional map. The image may be output as a two-dimensional representation of the activation map.

The machine-learned generative network may be an image-to-image convolutional deep learned network, such as an encoder-decoder convolutional network. Other network structures may include a convolution layer outputting a first plurality of spatial features to a global averaging layer, which outputs to a linear-sigmoid activation layer. For each location, the activation map is generated as a weighted sum from each of the first plurality of spatial features where weights of the weighted sum are from the global averaging layer. The spatial features may be for features from a last convolution layer of the machine-learned generative network.

In one embodiment, the machine-learned generative network was trained with ground truth for a binary classification of COPD or not for samples of second imaging data. For example, the machine-learned generative network was trained with the ground truth being from measures using a breath tube in a pulmonary function test and/or was trained with only a binary classification for loss. The machine-learned generative network was trained without any loss for the activation map.

In a second aspect, a system is provided for COPD classification. A medical scanner is configured to scan lungs of a patient. The scan results in image data representing the lungs of the patient. An image processor is configured to generate, with a machine-learned network including an encoder and a decoder, a spatial distribution of level of COPD by location in the lungs from the image data. A display is configured to display an image as a function of the spatial distribution of the level of COPD.

The medical scanner may be a computed tomography scanner including the image processor. The machine-learned network may be a generative network trained to output a value for COPD classification for the lungs. In one embodiment, the image processor is configured to generate based on features of the decoder where the machine-learned network was trained without a loss for the spatial distribution. In another embodiment, the machine-learned network was trained with a loss based only on the value for the COPD classification having a ground truth from a pulmonary function test.

In a third aspect, a method is provided for COPD classification in a medical imaging system. A map representing spatial distribution of COPD in the lungs of a patient is generated from intermediary features from an image-to-image network having been trained with deep learning to classify for COPD from pulmonary function test results. The map is displayed.

In one embodiment, the intermediary features are from a last convolution layer of the image-to-image network. In another embodiment, the map is generated as a weighted sum from the intermediary features where weights of the weighted sum are from a global averaging layer of the image-to-image network.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

COPD classification uses weakly supervised detection of abnormal regions. A model for classification as well as detection of regions of interest in COPD is created without the availability of image-based CT annotations for training. A score obtained from a pulmonary function test (e.g., the GOLD score) is used to classify high-resolution CT scans as having COPD or being healthy in the machine training. A 3-D U-net architecture learns to perform this classification. The last convolution layer of the network is used to automatically identify regions of importance, using the concept of class activation maps. The trained network is used to classify COPD from clinically acquired CT imaging, providing automatic detection of regions of importance for COPD.

Figure 1:
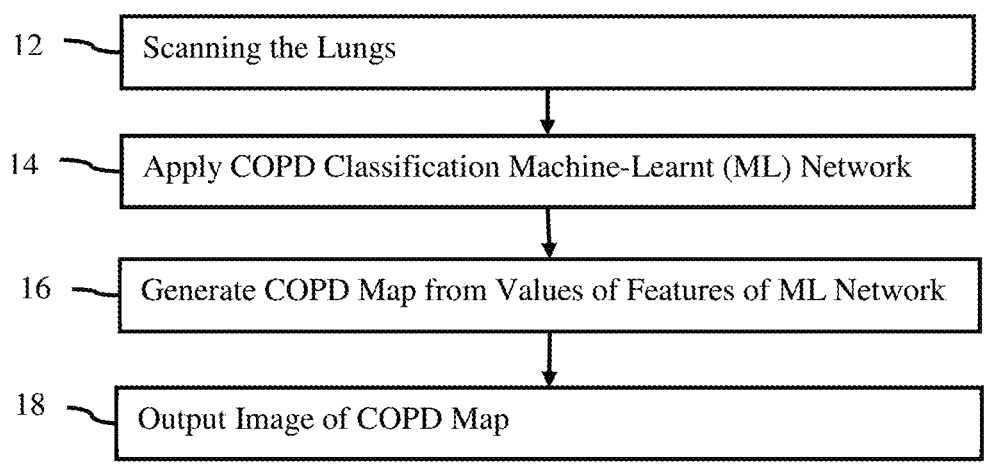
FIG. 1 is a flow chart diagram of one embodiment of a method for COPD classification in a medical imaging system.

FIG. 1 shows a method for COPD classification in a medical imaging system. The features from a deep machine-learned classifier are used to determine a spatial distribution of COPD level from an input medical scan.

The method of FIG. 1 is implemented in the order shown (e.g., top to bottom or numerical) or a different order. Additional, different, or fewer acts may be performed. For example, act 18 may be omitted. As another example, acts 14 and 16 may be performed without performing act 12, such as where scan data is loaded from memory. Acts for configuring the scanner, other medical imaging, and/or diagnosis workflow may be provided.

The method is implemented by a medical imaging system, such as any system for image processing from medical scans. The medical imaging system may be medical diagnostic imaging system, a review station, a workstation, a computer, a picture archiving and communication system (PACS) station, a server, a mobile device, combinations thereof, or another image processor. For example, the system shown in or described for FIG. 5 implements the method, but other systems may be used. A hardware image processor of any type of system, interacting with memory (e.g., PACS database or cloud storage), display, and/or medical scanner, may perform the acts.

The acts may be performed automatically. The user causes the patient to be scanned or obtains scan data for the patient from a previous scan. The user may activate the process. Once activated, the activation map with or without a non-spatial classification is generated and output to a display or medical record. User input of locations of the anatomy in any of the scan data may be avoided. Due to the generative network being trained on many samples using pulmonary function or other generalized lung performance test, the COPD activation map may be generated with greater accuracy than relying on a fewer number of annotated activation maps for training. Some user input may be provided, such as to confirm accuracy or perform diagnosis.

In act 12, a medical scanner scans the lungs of a patient. Herein, plural lungs are used, but a single lung or partial lung may be scanned. The medical scanner generates imaging data representing an interior of a patient. The image or imaging data is made available by or within the medical scanner. Alternatively, the acquisition is from storage or memory, such as acquiring a previously created dataset from a PACS. A processor may extract the data from a PACS or a medical records database.

The data may be in any format. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The imaging data is a dataset that may be used for imaging, such as scan data or a generated image representing the patient.

Any type of medical imaging data and corresponding medical scanner may be used. In one embodiment, the imaging data is a computed tomography (CT) image acquired with a CT system. For example, a chest CT dataset may be acquired by scanning the lungs using an x-ray source and detector mounted to a moveable gantry. For CT, the raw data from the detector is reconstructed into a three-dimensional representation by an image processor. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. The polar coordinate data is detected and beamformed into ultrasound data representing the patient.

The medical imaging data represents tissue and/or bone structure of the patient. For imaging the lungs, the imaging data may include response from the lungs and the anatomy around the lungs (e.g., upper torso). The data representing the lungs may be segmented so that data representing other parts of the patient is not included. The medical imaging or scan data may be normalized for scale and/or dynamic range.

The medical imaging data represents a multi-dimensional region of the lungs, such as a two or three-dimensional region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a 4D representation of the patient.

In one embodiment, imaging data is acquired for both inspiratory and expiratory scans. Inspiratory scans show emphysema by evaluating low-attenuation areas. Expiratory scans may be used to detect both emphysema and small airway disease, which is not as clearly visible in the inspiratory scans via gas-trapping regions (<−850 HU). In one embodiment, expiratory scans with 3 mm resolution are used for the training and classification task since the classification is to be generic to both main types of COPD. Imaging data from higher or lower resolution scans may be used. In other embodiments, only expiratory scans, only inspiratory scans, or scans at other times in the breathing cycle are used.

In act 14, an image processor applies a machine-learned generative network to the imaging data. The imaging data is input to the machine-learned generative network. The application results in creation of values for one or more spatial features learned to indicate COPD class. The class may be binary, such as having COPD or not, or may include three or more groups, such as GOLD score of 0-4.

The machine-learned generative network generates values for features in a two or three-dimensional distribution. The generated features may have the same and/or different spatial resolution as the input imaging data.

Any machine-learned generative network may be used. The generative network is an image-to-image convolutional deep-learned network. An image is input, and a synthetic image is generated, such as in the form of learned spatial features based on deep-learned convolutions, pooling, averaging, connections, weights, and/or other operations. For application of the learned generative network, the network only takes the imaging data as input, but other inputs may be provided, such as clinical data of a patient.

The generative network encodes the imaging data to a few independent latent variables and generates synthetic data by sampling the latent variables. In deep learning, the latent variables and synthetic data generation are learned by machine training. The generative network returns a prior log-likelihood and is implemented as a piecewise-differentiable function, such as used in deep learning. For example, the generative network is a deep learned model using restricted Boltzmann machines, deep belief network, neural autoregressive density estimators, variational auto-encoders, extensions thereof, or other deep learning approaches for generative modeling. In one embodiment, the trained deep generative network is a deep neural network with a set of j convolutional layers and k fully connected layers, each followed by a non-linear activation function, a set of pooling layers for features reduction, and a set of upscaling layers for image generation. Other layer arrangements may be used.

Figure 2:
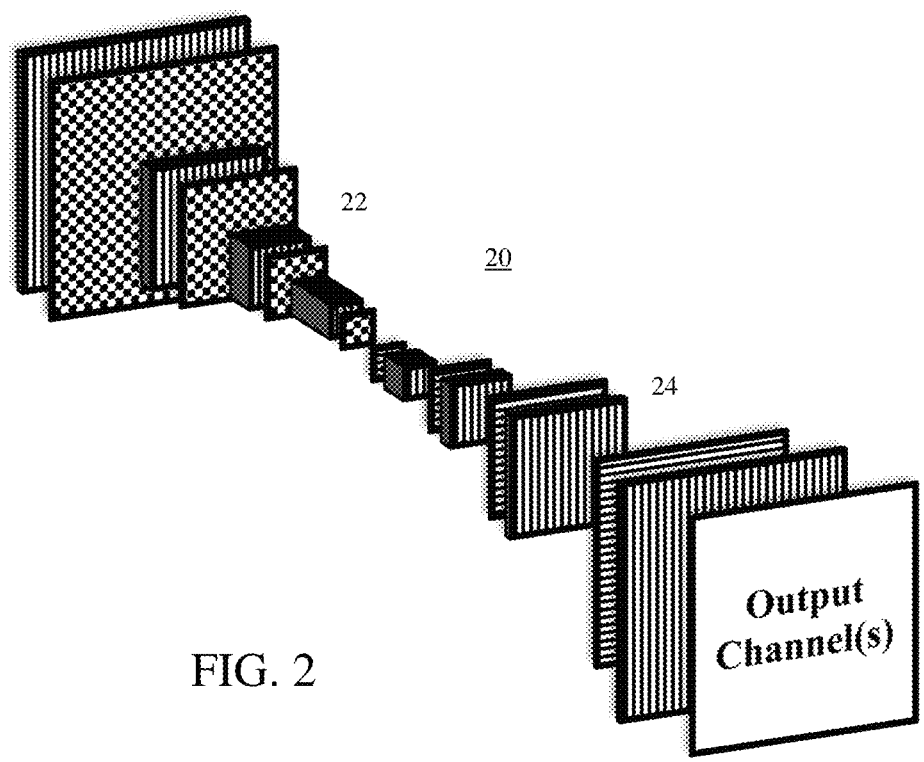
FIG. 2 is an example generative network.

In one embodiment, the machine-learned generative network is an encoder-decoder-based convolutional network. FIG. 2 shows one embodiment of a layer architecture for part of the generative network 20. Various convolution layers are arranged in an encoder 22, which outputs to a decoder 24. The encoder reduces the resolution from the input, providing greater and greater abstraction. The number of features may or may not increase as the resolution decreases. A bottleneck connects the output of the encoder 22 to the input of the decoder 24. The bottleneck may be direct or may include one or more layers, such as a convolutional layer. The decoder 24 reduces the amount of abstraction, such as up sampling and concatenating as part of convolution. The number of features may or may not be decreased with the increase in resolution. The output channels are the spatial features at the final layer of the decoder 24. Other encoder-decoder or image-to-image networks may be used.

The input imaging data may be a 2D slice, 3D slab, 3D volume, or a 4D volume over time. Any number of output channels (i.e., number of output spatial features) may be provided. Each output channel represents a synthetic image (e.g., a final or greatest resolution spatial feature of the decoder 24).

The image-to-image network is trained to generate the spatial features. Since a spatial distribution of COPD may not be available as ground truth for the training, another ground truth is used, such as pulmonary function test results or COPD diagnosis mined from a medical record. The ground truth may not be a spatial distribution. The machine-learned generative network architecture includes one or more layers trained use the spatial features to determine class membership. For example, a fully connected layer, pooling layer, maximum pooling layer, global averaging pooling layer, linear-sigmoid layer, SoftMax layer, and/or other layers connect in any order and/or with any number of layers after the output channels of the image-to-image network of FIG. 2.

Figure 3:
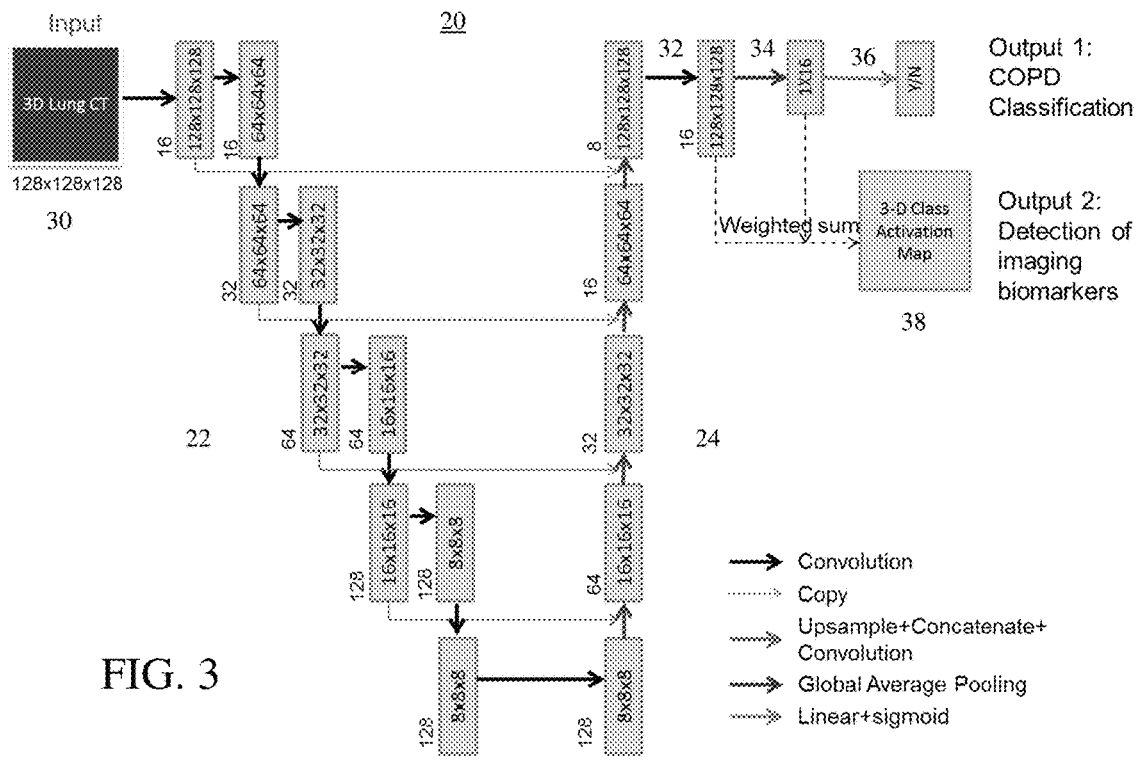
FIG. 3 is an example generative network for COPD classification.

FIG. 3 shows one example machine-learned generative network 20. The network is a deep image-image architecture based on the U-net segmentation architecture formed by the encoder 22 and decoder 24. The input to this network is a normalized, three-dimensional lung CT scan 30, shown as a 128×128×128 volume (other sizes may be used). The encoder 22 has 10 convolutional layers represented by bold black arrows, including a convolution layer at the bottleneck. Other numbers of convolution layers may be used. 16 input channels or features output by the first convolution layer are provided, but other numbers of features may be used. Two convolution layers are provided per level of abstraction or resolution so that the 16 input channels result in 128 features at the output of the encoder 22.

The decoder 24 includes four de-convolutional layers represented by the vertical arrows. Deconvolution is achieved by up-sampling and applying convolution. The 128 features from the bottleneck are up sampled and concatenated in deconvolution to form 8 features at a resolution of the input scan 30. Other numbers of features and/or layers may be used.

FIG. 3 shows skip connections from the encoder 22 to the decoder 24. Before each de-convolution operation, corresponding channels from the encoder 22 are concatenated to the up-sampled channels from the previous layers. Other numbers of skip connections, including no skip connections, may be used.

Three additional layers are included in the network 20. A convolution layer 32, global average layer 34, and linear-sigmoid layer 36 are provided. Additional, different, or fewer layers for classification may be provided. These additional layers are trained for classification from the learned spatial features.

The machine-learned generative network 20 has a convolution layer 32 outputting a plurality of spatial features. The decoder 24 is followed by the final convolution layer 32, with a 16-channel output, which is of the same size (e.g., resolution) as the input image 30. The 8 spatial features output by the decoder 24 are convolved to form 16 spatial features at a same resolution. Other numbers of features, resolutions, and/or layers may be provided.

The convolution layer 32 outputs to a global averaging layer 34. A global average pool is applied to the final convolution layer 32. The global averaging layer 34 converts the 16 spatial features into 16 values, such as averaging the values of each feature with weights learned in machine training. Other connections or pooling may be used.

The global averaging layer 34 outputs to a linear-sigmoid activation layer 36 (e.g., a linear layer and a sigmoid output activation). In alternative embodiments, a SoftMax or other classification layer is used. The 16 values of the global averaging layer 32 are combined to output whether the patient has COPD or not (i.e., binary classification). Alternatively, a fully connected or other layer is used to output probability of membership in more than two classes, such as 5 classes of the GOLD score.

Additional, different, and/or fewer layers or types of layers may be used for the generative network, encoder 22, decoder 24, or classifier layers (e.g., 32, 34, and 36). Skip connects (i.e., feeding features forward to non-adjacent layers), feedback, and/or max pooling indices may be used.

The machine-learned generative network is trained with ground truth for the classification. The binary or multiple-level COPD classification generalized to the patient or lung rather than a spatial distribution is used as the ground truth for training the network. Each sample CT scan or imaging data is labeled with a ground truth diagnosis or measure for COPD generic to the type of COPD. For example, the ground truth is from measures using a breath tube (inhalation or exhalation measures) in a pulmonary function test. The GOLD scores may be used. The GOLD score for each sample is thresholded to find a binary classification of COPD or not (e.g., 0=no COPD and 1-4=COPD). Alternatively, the COPD score is used as the ground truth to classify into one of five classes (0-5 GOLD score).

Activation maps are not used as ground truth. A spatial distribution is not used to determine a loss in training. Instead, the generative network is trained to estimate the class membership globally or for the whole scan region of the lung. Spatial features may be learned to better determine that class membership but are used to determine a non-spatial classification based on ground truth of more commonly available COPD diagnosis or measurement. The spatial features are learned in this weakly supervised manner.

For training the generative network, a computer, workstation, server, or other processor accesses a database of hundreds or thousands of example images with known COPD diagnosis (e.g., yes/no or GOLD score). The machine learns the generative network from the images and ground truth of the database. Using a piecewise-differentiable function or other deep learning function, the machine trains the deep generative network to learn spatial features and classification from the learned spatial features to output the classification.

To train the generative model, the log-likelihood of the output is maximized. The generative model encodes spatial features (i.e., kernels of the convolution layers). The generative network is trained with deep machine learning to output the class membership. The network parameters (e.g., machine trained features, kernels, connections, weights, or layer values) are learned.

Any loss function, such as L1 or L2, may be used. The loss function may be for binary classification for loss, such as a L1 loss based on correct estimation as the patient having COPD or not. The loss function may be for any number of classes. There is no loss function used for activation maps or spatial distribution of COPD. Any optimization, such as Adam or Ada, may be used in training using the training data and loss function.

The learned network is stored in the memory with the training data or other memory. For example, copies of the learned network are distributed to or on different medical scanners for use in hospitals or medical practices. As another example, copies are stored in a memory of one or more servers for COPD diagnosis assistance as a service or for remote COPD diagnosis assistance.

In alternative embodiments, the machine-learned network is trained to classify for the type of COPD. Image-level (e.g., patient or global classification) labels or ground truth for subtype of COPD (e.g., emphysema verses airway disease) are used in training. The classes may be the various subtypes and no COPD (e.g., three classes for emphysema, airway disease, and no COPD). Through training for classification, the learned spatial features may better distinguish between types of COPD. In yet other embodiments, the network includes long-short term memory units where a sequence of image data acquired from a patient at different times is used.

In act 16 of FIG. 1, the image processor generates a map representing spatial distribution of COPD in the lungs of a patient. The map represents, by location, a level of COPD. Any resolution of levels may be used, such as two, three, four, five, or more. The number of levels of COPD may be different than the number of classes used to train the machine-learned generative network. The map represents a spatial distribution in two or three dimensions (i.e., a multi-dimensional region) of the patient's lungs. For example, a three-dimensional map of COPD is generated. For each pixel or voxel, a level of COPD for the represented location is generated.

The machine-learned generative network is not trained to generate the map. For example, the network is trained to classify an estimate of the pulmonary function test result given input CT scan data. The map is generated from spatial features learned for classification of COPD. Any spatial distribution features may be used. Since the features are deep learned to distinguish between global COPD classes as part of a class activation, the features themselves reflect level of COPD by location.

Any intermediary features of the machine-learned generative network may be used. For example, any of the features from the encoder, decoder, and/or classifier may be used. The features are intermediary to the output classification. A subset of features or all features from one layer or multiple layers may be used. In response to application of the imaging data to the machine-learned network, values for the various spatial features are generated for classification. The values for any spatial distribution feature are then used to generate the COPD activation map. The deep-learned features from the image-to-image network, including the classifier, are used.

Any combination of values of one or more features is used to generate the map. For example, a single feature provides values by spatial location. The values for this feature are used as the map. As another example, the values for all or a sub-set of features from a convolution layer or layers of the generative network are combined, such as averaged. For each location, the values from the different features are combined. Values from features at different layers may be used, such as after interpolation, up-sampling, or down-sampling.

For each location, any combination may be used. For example, a weighted sum or average may be used. Any weights, such as empirically selected weights, may be used. Ratio, minimum, maximum, or other combination may be used.

The combination is hand coded. Rather than learning to combine to generate the map, programmer created software instructions combining the values are used. In alternative embodiments, the network is trained to combine to generate of the activation map, such as by multi-task learning.

FIG. 3 shows one embodiment of the combination. A weighted sum of the values from the features in the last convolution layer 32 is used. The final convolution layer 32 is used to obtain a class activation map 38, which highlights features of importance in each input scan. Each of the 16 channels in the last convolution layer 32 contributes to the class activation map 38. For each location, the 16 values from the 16 features are weighted, and the weighted results are summed. The weights are the values in the vector output by the global averaging layer 34. These weights represent a learned contribution of each spatial distribution feature to the classification.

The activation of location (x,y,z) in each channel k, corresponds to the voxel at location (x,y,z) in the input image. $f_k(x,y,z)$ is denoted as the activation of voxel (x,y,z) in channel k. This layer is followed by a global average pool, therefore the output of each channel k is $O_k=f_k(x,y,z)$. This layer is followed by a linear layer with weights $w_k$, with output given by a sigmoid function. The output y of the classification generative network can be written as:

$$y = \sigma\left(\sum_1^{16} w_k O_k\right) = \sigma\left(\sum_1^{16} w_k \sum_{x,y,z} f_k(x, y_j z)\right) = \sigma\left(\sum_{x,y,z} \sum_1^{16} w_k f_k(x, y, z)\right)$$

The class activation map is denoted by M, where $M(x,y,z) = \Sigma_1^{16} w_k f_k(x,y,z)$, and thereby the output $y=\sigma(\Sigma_{x,y,z} M(x,y,z))$. The activation of M at each location (x,y,z) therefore directly corresponds to the importance of voxel (x,y,z) of the input image in the prediction of COPD. Other functions may be used.

In act 18 of FIG. 1, the image processor outputs an image on a display. A representation of the activation map or data derived from the activation map is displayed. For display, the image is formed as a two-dimensional image of pixels in the display format. Alternatively, the image is output to a memory or patient medical record for later viewing.

The map is displayed. An image is generated from the activation map. Where the activation map represents a volume, the values for the voxels are rendered to pixel values. Any volume rendering may be used, such as alpha blending, projection, maximum intensity projection, or cinematic rendering. Alternatively, a slice or plane is defined in the volume, and the pixel values in the slice or plane are selected or interpolated from the nearest voxels.

The gray scale level for each pixel is modulated according to the level of COPD in the activation map. Alternatively, the color is selected or controlled according to the level of COPD in the activation map.

Figure 4:
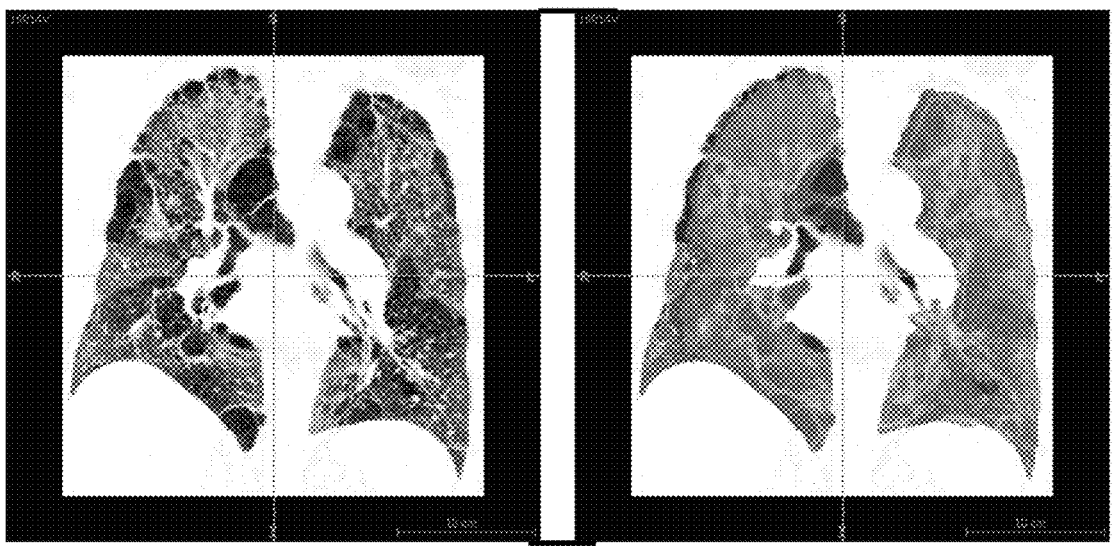
FIG. 4 illustrates an example lung image and an example image of a COPD activation map.

FIG. 4 shows two example images. The image on the left is an image of a coronal plane for an input CT scan. The image on the right is the class activation map obtained from the generative network of FIG. 3 using the weighted sum. The activations are overlaid on the input scan for clarity. The class activation map shows highly significant regions darker and regions with low significance lighter. The combination of values from features of the generative network automatically detects COPD affected regions, such as low-attenuation areas showing lung tissue destruction. The physician is assisted by knowing where to examine the CT image more closely and/or by the distribution of COPD locations. This information may assist in confirming COPD and/or distinguishing between types of COPD.

The image may include an alphanumeric or graphical representation of the classification, such as the non-spatial or global estimate output by the machine-learned network. Both the estimated classification and the image of the activation map are displayed.

The scan data may be used to generate an image of the lungs. The image may be a cross-section through the lungs. Alternatively, the image is a rendering of the three-dimensional distribution to a two-dimensional display, 3D holographic display, an augmented reality display, or virtual reality display. The activation map is displayed adjacent to or overlaid on the CT image.

In one example, the generative network of FIG. 3 is trained and tested. The training dataset is obtained from the COPDgene cohort, which includes imaging and clinical data of 10,306 subjects with and without COPD. Based on a GOLD score classification, 3311 of these subjects have COPD, 6247 of them are healthy and the status of 748 subjects is unknown. 53% of this cohort is male, and the overall age distribution of the cohort is 59.54±9.05 years. Both inspiratory and expiratory scans are present for the subjects in the COPDgene cohort. Expiratory scans with 3 mm resolution are used for the training and classification to discover both main types of COPD.

The model of FIG. 3 is compared to a logistic regression using deep learning from CT-based measurements of COPD calculated by computing low-attenuation areas. For each input expiratory scan, the following metrics are computed to be the input feature vector for the logistic regression: percentage of low-attenuation area in the whole lung (<−850 HU), percentage of low-attenuation area in each lung lobe (<−850 HU), the mean, maximum and minimum volumes of low-attenuation regions, the mean, maximum and minimum intensities of low-attenuation regions, and the total lung volume. Using different machine learning methods, different models are generated to predict COPD based on these features. A straightforward logistic regression has the best performance with an AUC of 0.87.

The model of FIG. 3 is compared to deep learning with a convolutional neural network. Training using a convolutional neural network (i.e., 3D Res50 architecture) that had been pre-trained on videos from the Kinetics dataset is performed. The model is trained with 3D lung CTs in three different ways: (1) the model is trained with the axial plane as the in-plane image input to the video network, with slices from top to bottom considered as "time," (2) the model is trained with the sagittal plane as the in-plane image input to the video network, with slices from left to right considered as "time," and (3) the model is trained with the coronal plane as the in-plane image input to the video network, with slices from front to back considered as "time." The ensemble of these three models gives the best result of AUC 0.91.

The generative network (i.e., UNET+GAP architecture) of FIG. 3 out-performs both the logistic regression from the metrics and the ensemble using the convolutional neural network. The generative network of FIG. 3 has an AUC of 0.93.

The model of FIG. 3 is compared to other computed assisted diagnosis (CAD) models in COPD. Most of image processing and CAD models focus on classifying emphysema from healthy controls or classifying different types of emphysema. COPD includes various subtypes. Since COPD is a heterogeneous condition, CAD models that focus of emphysema are unable to detect mild cases of COPD with no visible emphysema but have small airway disease present. In addition, these CAD models are also unable to assess the relative contribution of emphysema and airway disease to the condition. The knowledge of relative contribution of the different disease subtypes is useful in the clinic for prognosis prediction and managing a therapy plan. By providing an activation map, the model of FIG. 3 provides information that may be used to better assess the relative contribution.

The model of FIG. 3 can predict all cases of COPD, including those with a mild condition. Early detection of mild COPD may be provided, enabling patients to start therapies for disease management in early stages.

The activation map provides automated detection of regions of importance and is interpretable and generalizable. Regions of interest in input CT lung scans are detected without explicit image annotations in the machine training. This increases interpretability of the results of a deep learning network, which are usually considered to be black-box methods. This also will contribute to increased confidence and clarity by clinicians and radiologists.

While used for COPD, the architecture may be adapted to a wide range of medical problems that lack explicit image annotations but have some meta-information or image-level information regarding the disease diagnosis or staging. The image-level labels (i.e., one class for the entire scan region) may be used to train and interpret the input scans in a wide range of CAD tasks such as: detection and classification of lung nodules, prostate lesions, breast cancer, brain tumors, liver tumors, and so on.

Figure 5:
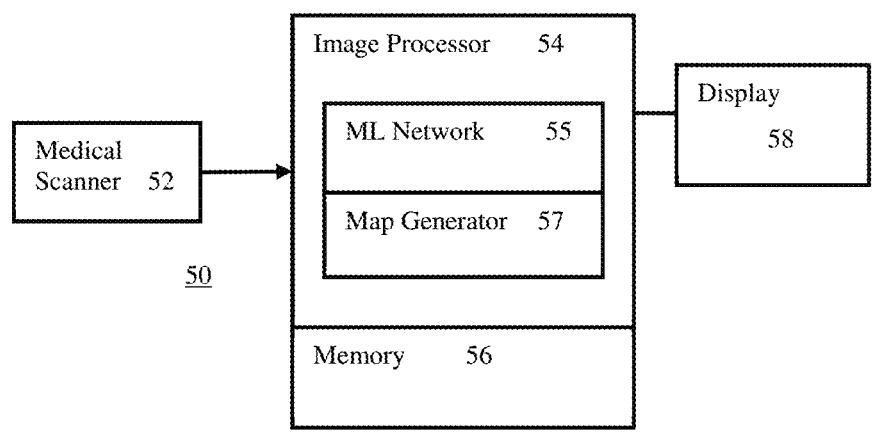
FIG. 5 is a block diagram of one embodiment of a system for COPD classification.

FIG. 5 shows a system 50 for COPD classification. The system 50 implements the method of FIG. 1 or another method. The system 50 is for application of a machine-learned generative network. Given input imaging data, the system 50 uses the generative network to generate a COPD map from values of learned spatial features used to classify. While the system 50 is described below in the context of application of the previously learned generative network, the system 50 may be used to machine train the generative network.

The system 50 includes an image processor 54, a memory 56, a display 58, and a medical scanner 52. The image processor 54, memory 56, and display 58 are shown separate from the medical scanner 52, such as being part of a workstation, computer, or server. In alternative embodiments, the image processor 54, memory 56, and/or display 58 are part of the medical scanner 52. In yet other embodiments, the system 50 does not include the medical scanner 52. Additional, different, or fewer components may be used.

The medical scanner 52 is a CT, MR, ultrasound, camera, or other scanners for scanning a lung of a patient. In one embodiment, the medical scanner 52 is a CT system with an x-ray source and detector mounted to a moveable gantry for three-dimensional scanning of the upper torso of the patient. The image processor 54 or other processor of the medical scanner 52 performs computed tomography to determine scalar values for the tissue response to the x-rays in three dimensions.

The scan provides the scan data representing the lungs. The medical scanner 52 is configured by user settings or presets to scan the lungs of the patient, resulting in scan data representing all or at least part of the lungs of the patient. This imaging data is in any format, such as scalar values distributed in a regular or evenly dispersed 3D grid (i.e., uniform voxels).

The memory 56 is a buffer, cache, RAM, removable media, hard drive, magnetic, optical, database, or other now known or later developed memory. The memory 56 is a single device or group of two or more devices. The memory 56 is shown associated with or part of the image processor 54 but may be outside or remote from other components of the system 50. For example, the memory 56 is a PACS database storing the scan data from the medical scanner 52.

The memory 56 stores the scan data, a machine-learned generative network 55, a map generator 57, values of features, activation map, image, and/or information used in image processing to generate the activation map. For example, the activation map and classification for stored imaging data are stored. For training, the training data (i.e., scan data and ground truth measurement, score, or diagnosis) are stored in the memory 56.

The memory 56 is additionally or alternatively a non-transitory computer readable storage medium with processing instructions. The memory 56 stores data representing instructions executable by the programmed image processor 54. The instructions for implementing the processes, methods and/or techniques discussed herein are provided on computer-readable storage media or memories, such as a cache, buffer, RAM, removable media, hard drive or other computer readable storage media. The machine-learned generative network may be stored as part of instructions for classification or map generation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 54 is a general processor, digital signal processor, three-dimensional data processor, graphics processing unit, application specific integrated circuit, field programmable gate array, digital circuit, analog circuit, artificial intelligence processor, combinations thereof, or other now known or later developed device for generating an activation map by application of a machine-learned classifier or network 55. The image processor 54 is a single device, a plurality of devices, or a network. For more than one device, parallel or sequential division of processing may be used. Different devices making up the image processor 54 may perform different functions, such as one processor applying the machine-learned network 55 and another processor using the map generator 57 to generate the activation map from values of features resulting from the application of the machine-learned network 55. In one embodiment, the image processor 54 is a control processor or other processor of a medical diagnostic imaging system (e.g., medical scanner 52). The image processor 54 is a hardware device configured by or operating pursuant to stored instructions, design (e.g., application specific integrated circuit), firmware, or hardware to perform various acts described herein.

The image processor 54 is configured to generate, with a machine-learned network 55 including an encoder and a decoder, a spatial distribution of level of COPD by location in the lungs from the image data. In response to input of the image data representing the lungs of the patient to a generative network 55 trained to output a value for COPD classification for the lungs, the image processor 54 generates a class activation map with the map generator 57. Features of the decoder are used to generate the map even where the machine-learned network 55 was trained without a loss for the spatial distribution (i.e., no ground truth for spatial distribution of COPD). For example, the machine-learned network 55 was trained with a loss based only on the value for the COPD classification having a ground truth from a pulmonary function test.

The image processor 54 may generate an image. The generated map, classification, and/or imaging data are used to generate an image. The image is of the lungs of the patient with highlighting or relative indication COPD level of different parts. The image provides added visualization of the locations contributing to COPD diagnosis.

The display 58 is a CRT, LCD, plasma, projector, printer, or other output device for showing an image or other output of the image processor 54 and/or medical scanner 52. The display 58 displays an image that is a function of the spatial distribution of the level of COPD. The image may be the activation map overlaid as color or brightness on a CT image of the lungs or part of the lungs. The image may include an annotation for the image or scan region level, global or patient general estimate of COPD diagnosis and/or severity.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for chronic obstructive pulmonary disorder (COPD) classification in a medical imaging system, the method comprising:

scanning, by a medical scanner, lungs of a patient, the scanning providing first imaging data representing a multi-dimensional region of the lungs of the patient;

applying, by an image processor, a machine-learned generative network to the first imaging data, the machine-learned generative network trained to output the COPD classification;

generating an activation map from values of features from the machine-learned generative network, the activation map representing a level of COPD by location within the multi-dimensional region; and outputting, on a display, an image from the activation map.

2. The method of claim 1 wherein scanning comprises scanning with the medical scanner being a computed tomography system, wherein the multi-dimensional region comprises a three-dimensional region, and wherein the activation map is a three-dimensional map.

3. The method of claim 1 wherein applying comprises applying the machine-learned generative network as an image-to-image convolutional deep learned network.

4. The method of claim 1 wherein applying comprises applying the machine-learned generative network as an encoder-decoder convolutional network.

5. The method of claim 1 wherein applying comprises applying the machine-learned generative network having a convolution layer outputting a first plurality of spatial features to a global averaging layer, which outputs to a linear-sigmoid activation layer.

6. The method of claim 5 wherein generating the activation map comprises, for each location, a weighted sum from each of the first plurality of spatial features where weights of the weighted sum are from the global averaging layer.

7. The method of claim 1 wherein generating the activation map comprises generating based on values for features from a last convolution layer of the machine-learned generative network.

8. The method of claim 1 wherein applying comprises applying the machine-learned generative network as having been trained with ground truth for a binary classification of COPD or not for samples of second imaging data.

9. The method of claim 8 wherein applying comprises applying the machine-learned generative network as having been trained with the ground truth being from measures using a breath tube in a pulmonary function test.

10. The method of claim 8 wherein applying comprises applying the machine-learned generative network as having been trained with only the binary classification for loss.

11. The method of claim 1 wherein applying comprises applying the machine-learned generative network as having been trained without any loss for the activation map.

12. The method of claim 1 wherein outputting comprises outputting the image as a two-dimensional representation of the activation map.

13. A system for chronic obstructive pulmonary disorder (COPD) classification, the system comprising:

a medical scanner configured to scan lungs of a patient, the scan resulting in image data representing the lungs of the patient;

an image processor configured to generate, with a machine-learned network comprising an encoder and a decoder, a spatial distribution of level of COPD by location in the lungs from the image data; and a display configured to display an image as a function of the spatial distribution of the level of COPD.

14. The system of claim 13 wherein the medical scanner comprises a computed tomography scanner including the image processor.

15. The system of claim 13 wherein the machine-learned network comprises a generative network trained to output a value for COPD classification for the lungs.

16. The system of claim 15 wherein the image processor is configured to generate based on features of the decoder where the machine-learned network was trained without a loss for the spatial distribution.

17. The system of claim 15 wherein the machine-learned network was trained with a loss based only on the value for the COPD classification having a ground truth from a pulmonary function test.

18. A method for chronic obstructive pulmonary disorder (COPD) classification in a medical imaging system, the method comprising:
   generating a map representing spatial distribution of COPD in the lungs of a patient, the map generated from intermediary features from an image-to-image network having been trained with deep learning to classify for COPD from pulmonary function test results;
   displaying the map.

19. The method of claim 18 wherein generating comprises generating the map where the intermediary features are from a last convolution layer of the image-to-image network.

20. The method of claim 18 wherein generating comprises generating as a weighted sum from the intermediary features, weights of the weighted sum being from a global averaging layer of the image-to-image network.

* * * * *